United States Patent
Anne-Archard et al.

(10) Patent No.: US 6,916,929 B2
(45) Date of Patent: Jul. 12, 2005

(54) METHOD FOR PREPARING 4-METHYLAMINO-4-PHENYLPIPERIDINE

(75) Inventors: Gilles Anne-Archard, Toulouse (FR); Patrick Gros-Claude, Berberaud (FR)

(73) Assignee: Sanofi-Synthelabo, Paris (FR)

( * ) Notice: Subject to any disclaimer, the term of this patent is extended or adjusted under 35 U.S.C. 154(b) by 12 days.

(21) Appl. No.: 10/483,475

(22) PCT Filed: Jul. 15, 2002

(86) PCT No.: PCT/FR02/02498

§ 371 (c)(1),
(2), (4) Date: Jan. 12, 2004

(87) PCT Pub. No.: WO03/008381

PCT Pub. Date: Jan. 30, 2003

(65) Prior Publication Data

US 2004/0181071 A1 Sep. 16, 2004

(30) Foreign Application Priority Data

Jul. 16, 2001 (FR) .............................. 01 09575

(51) Int. Cl.$^7$ .......................................... C07D 211/58
(52) U.S. Cl. .................................................. 546/224
(58) Field of Search ........................................ 546/224

(56) References Cited

U.S. PATENT DOCUMENTS 6,716,846 B2 * 4/2004 Tulshian et al. ....... 514/253.01

OTHER PUBLICATIONS

Wilson, W., Journal of the Chemical Society, London, pp. 2173–2176 (1950).
Kalir, Pelah, Israel Journal of Chemistry, vol. 5, pp. 223–229 (1967).

* cited by examiner

*Primary Examiner*—Kamal A. Saeed
(74) *Attorney, Agent, or Firm*—Balaram Gupta

(57) ABSTRACT

The invention relates to a process for preparing a 4-alkoxycarbonylamino-1-benzyl-4-phenylpiperidine of formula (I)

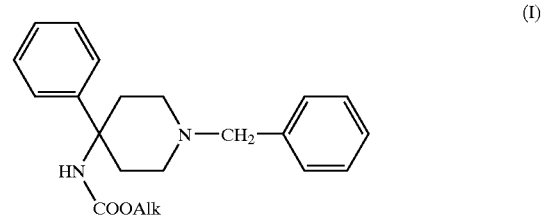

via hydrolysis of 1-benzyl-4-cyano-4-phenylpiperidine (II) in acidic medium and treatment of the 1-benzyl-4-phenyl-4-piperidinecarboxamide (III) thus obtained with bromine in the presence of an alkali metal alkoxide.

The invention also relates to a process for preparing 4-methylamino-4-phenylpiperidine from compound (II).

6 Claims, No Drawings

METHOD FOR PREPARING 4-METHYLAMINO-4-PHENYLPIPERIDINE

The present invention relates to a process for preparing 4-methylamino-4-phenylpiperidine and its salts. 4-Methylamino-4-phenylpiperidine is an intermediate that is useful for preparing therapeutic active principles, for example tachykinin antagonists.

According to G. A. M. Giardina et al. (Bioorg. Med. Chem. Letters, 1996, 6, 2307–2310), 4-methylamino-4-phenylpiperidine can be prepared in six steps from 1-benzyl-4-piperidone via reaction with phenyllithium, treatment of the 1-benzyl-4-phenylpiperidin-4-ol thus obtained with sulfuric acid and acetic acid in acetonitrile, deacetylation of the 4-acetamido-1-benzyl-4-phenylpiperidine, formulation of the 4-amino-1-benzyl-4-phenylpiperidine, reduction of the N-formyl derivative thus obtained with lithium aluminum hydride and final debenzylation of the 1-benzyl-4-methylamino-4-phenylpiperidine via catalytic hydrogenation. Although these six steps turn out good yields, the process has drawbacks that make it difficult to apply industrially. More particularly, in the preparation of 4-methylamino-4-phenylpiperidine, two of the six steps are performed at reflux for three days which considerably lengthens the duration of the process. Furthermore, this preparation involves, in the first step, the use of phenyllithium, which may entail appreciable problems at the industrial level.

It has now been found that, starting with a readily available commercial product, 1-benzyl-4-cyano-4-phenylpiperidine, it is possible to obtain a 4-alkoxycarbonylamino-1-benzyl-4-phenylpiperidine in only two steps that may be performed in the same reactor ("one-pot" reaction) with an overall yield of at least 85%. The compound may then be converted into 4-methylamino-4-phenylpiperidine in a further two steps, which, themselves also, may be performed in the same reactor ("one-pot" reaction).

Thus, according to one of its aspects, the present invention relates to a process for preparing a 4-alkoxycarbonylamino-1-benzyl-4-phenylpiperidine of formula (I)

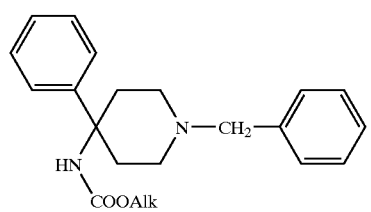

(I)

in which Alk represents an alkyl of 1 to 3 carbon atoms, characterized in that 1-benzyl-4-cyano-4-phenylpiperidine of formula (II)

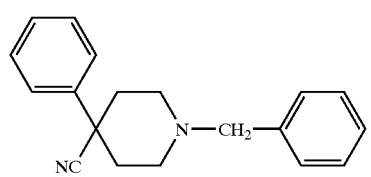

(II)

is hydrolyzed to the amide in acidic medium and the 1-benzyl-4-phenyl-4-piperidinecarboxamide thus obtained of formula (III)

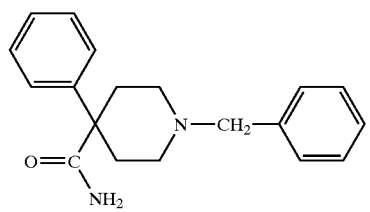

(III)

is treated with bromine in the presence of an alkali metal alkoxide of formula (IV)

$$\text{Alk-OM} \qquad \text{(IV)}$$

in which Alk is a $(C_1-C_3)$alkyl and M is an alkali metal.

The starting compound of formula (II) is a product that is commercially available in hydrochloride form, from which the base may be readily released via neutralization with an alkali metal hydroxide. 1-Benzyl-4-cyano-4-phenylpiperidine may be prepared in situ in the solvent used for the hydrolysis of the nitrile to the amide.

This hydrolysis to amide is preferably performed with sulfuric acid and acetic acid in an organic solvent, preferably a hydrocarbon such as toluene, at a temperature of 80–100° C. After heating for 4–8 hours, the reaction is complete and the 1-benzyl-4-phenyl-4-piperidinecarboxamide (III) is recovered in the organic phase and may be isolated.

Advantageously, the solution of compound (III) in the organic solvent, for example in toluene, is used directly for the rearrangement into compound (I). This rearrangement is performed in the same solvent via the action of bromine in the presence of an alkali metal alkoxide Alk-OM. The alkali metal alkoxide preferably used is sodium or potassium methoxide or ethoxide (formula IV, Alk=$CH_3$ or $C_2H_5$ and M=Na or K).

The addition of bromine takes place at a temperature of from −10 to +10° C., preferably at 0° C., and the reaction is complete after 6–20 hours at room temperature.

The 4-alkoxycarbonylamino-1-benzyl-4-phenylpiperidine thus obtained is isolated from the reaction mixture by addition of water, removal of the aqueous phase containing the reaction by-products, especially the mineral salts, and precipitation by addition of a suitable solvent. When the rearrangement takes place in toluene, xylene or benzene, the precipitation is induced via addition of an aliphatic or cycloaliphatic hydrocarbon, for example hexane, cyclohexane or methylcyclohexane, or in an ether such as isopropyl ether or methyl tert-butyl ether in which compound (I) is insoluble.

The 4-alkoxycarbonylamino-1-benzyl-4-phenylpiperidine (I) is obtained in a very high yield, calculated from the starting compound (II), normally of greater than 80%, and thus allows, for example, the synthesis of 4-methylamino-4-phenylpiperidine and its salts in only four steps, of which both the first two and the last two may be performed in the same reactor ("one-pot" reactions).

Thus, according to another of its aspects, the present invention relates to a process for preparing 4-methylamino-4-phenylpiperidine, characterized in that:

(a) 1-benzyl-4-cyano-4-phenylpiperidine of formula (II) is hydrolyzed to the amide in acidic medium and the 1-benzyl-4-phenyl-4-piperidinecarboxamide of formula (III) is treated with bromine and an alkali metal $(C_1-C_3)$ alkoxide; and then (b) the 4-$(C_1-C_3)$alkoxycarbonylamino-1-benzyl-4-phenylpiperidine thus obtained is reduced with a metal hydride, which may be a mixed hydride, or with Vitride® (sodium bis(2-methoxyethoxy)aluminum hydride as a 70% solution in toluene) and the 1-benzyl-4-methylamino-4-phenylpiperidine thus obtained, optionally in the form of one of its salts, is debenzylated via catalytic reduction and the 4-methylamino-4-phenylpiperidine thus obtained is isolated either in free base form or in the form of one of its salts and is optionally converted into the free base.

According to one very advantageous procedure, this process allows the preparation of 4-methylamino-4-phenylpiperidine and its pharmaceutically acceptable salts via reduction with lithium aluminum hydride or Vitride® of 1-benzyl-4-methoxycarbonylamino-4-phenylpiperidine, via debenzylation either with formic acid or under a hydrogen atmosphere, in the presence of palladium-on-charcoal or palladium-on-barium sulfate and isolation of the 4-methylamino-4-phenylpiperidine either in free base form or in the form of one of its salts, preferably in the form of dioxalate, which is optionally converted into the free base.

According to this very advantageous procedure, the reduction of the 1-benzyl-4-methoxy (or ethoxy) carbonylamino-4-phenylpiperidine may be performed with lithium aluminum hydride in tetrahydrofuran, at a temperature of between 20° C. and the reflux point of the reaction mixture. When the reduction is complete, the reducing agent is destroyed according to the conventional methods, for example with an aqueous solution of a common base: sodium hydroxide. After evaporating off the tetrahydrofuran, the 1-benzyl-4-methylamino-4-phenylpiperidine may be recovered by evaporation of the solvent and isolated, or alternatively, after evaporation of the solvent, it may be dissolved in a solvent such as hydrocarbon, especially in toluene, and the solution thus obtained may be used directly for the debenzylation.

The reduction of the 1-benzyl-4-methoxy (or ethoxy) carbonylamino-4-phenylpiperidine may be performed with Vitride®, preferably in toluene at a temperature of from 70 to 105° C. and preferably from 90° to 100° C., and then working as illustrated above, the 1-benzyl-4-methylamino-4-phenylpiperidine is recovered and isolated, or alternatively it may be subjected directly to debenzylation preferably in the toluene solution.

Thus, starting with 1-cyano-1-benzyl-4-phenylpiperidine hydrochloride, 4-methylamino-4-phenylpiperidine may be obtained in an overall yield of greater than 70%.

The best yields for the preparation of 4-methylamino-4-phenylpiperidine are obtained via a process characterized in that:

(a') 1-benzyl-4-cyano-4-phenylpiperidine, prepared in situ via neutralization of its hydrochloride, is treated with 94–96% sulfuric acid and acetic acid in toluene at 80–100° C. and the 1-benzyl-4-phenyl-4-piperidinecarboxamide thus obtained is treated with bromine in the presence of sodium methoxide; and then (b') the 1-benzyl-4-methoxycarbonylamino-4-phenylpiperidine thus obtained is reduced with Vitride® in toluene at a temperature of 90–100° C., the 1-benzyl-4-methylamino-4-phenylpiperidine thus obtained, or one of its salts, is debenzylated via hydrogenolysis, for example with formic acid in the presence of palladium, and the 4-methylamino-4-phenylpiperidine is isolated either in the form of the free base or in the form of one of its salts, which is optionally converted into the free base.

When the 4-methylamino-4-phenylpiperidine is isolated in the form of one of its salts, the preferred salts are the dioxalate and the sesquioxalate, optionally in hydrated form.

The EXAMPLES that follow illustrate the invention.

EXAMPLE 1

Benzyl-4-methoxycarbonylamino-4-phenylpiperidine (a) 1-Benzyl-4-phenyl-4-piperidinecarboxamide.

A mixture of 3 kg of commercial 1-benzyl-4-cyano-4-phenylpiperidine, 6 l of water, 8.98 l of toluene and 1.35 kg of an aqueous 35% sodium hydroxide solution is heated under nitrogen at 60° C. and the aqueous phase is separated out by settling at this temperature. The toluene phase is dried by azeotropic distillation and the solution thus obtained containing the 1-benzyl-4-cyano-4-phenylpiperidine base is added to a mixture of 2.83 kg of 95% sulfuric acid, 1.73 kg of glacial acetic acid and 3 l of toluene. The mixture thus obtained is heated for 6 hours, the heating is then stopped, the mixture is cooled to 60° C. and 3 l of water are added at this temperature. The mixture is allowed to cool to room temperature (about 20° C.) and is then poured into 8.65 l of 30% sodium hydroxide and 6.75 l of water. The temperature rises gradually to 75° C. The phases are separated by settling while hot and the organic phase is washed with water and dried azeotropically. The toluene solution is concentrated to half its volume and then cooled gradually to 60° C. and the crystallization is initiated. The crystallization is completed by cooling to 0° C. over 2 hours. The precipitate thus obtained is filtered off, washed and dried under vacuum at 60° C. 2.68 kg of 1-benzyl-4-phenyl-4-piperidinecarboxamide are thus obtained;

m.p.=117–118° C. Purity: 99%—yield: 95%.

(b) 1-Benzyl-4-methoxycarbonylamino-4-phenylpiperidine.

A sodium methoxide solution prepared from 4.52 l of methanol and 532 g of sodium is added over one hour and with stirring, at a temperature of –5° C., to a solution of 2.68 kg of the product obtained in step (a) in 10.7 l of toluene cooled to this temperature, and then, while maintaining the temperature at about 0° C., 1.85 kg of bromine are added. The reaction mixture is left for 30 minutes at 0° C. and then overnight at room temperature, and is subsequently washed with water at 60° C. The toluene solution is dried azeotropically and is then concentrated by distilling off 75% of the amount of toluene used, and is treated with 12 l of isopropyl ether. This mixture is cooled to 25° C. and then left to crystallize for 24 hours at this temperature and is finally cooled to 0° C. The product thus precipitated is filtered off, washed with isopropyl ether and dried under vacuum at 50° C. 2.62 kg of 1-benzyl-4-methoxycarbonylamino-4-phenylpiperidine are thus obtained with an HPLC purity of 99%. m.p.=121–122° C.

EXAMPLE 2

4-Methylamino-4-phenylpiperidine dioxalate (a) 1-Benzyl-4-methoxycarbonylamino-4-phenylpiperidine A mixture of 3 kg of commercial 1-benzyl-4-cyano-4-phenylpiperidine, 6 l of water, 8.98 l of toluene and 1.35 kg of aqueous 35% sodium hydroxide solution is heated under nitrogen at 60° C. and the aqueous phase is separated out by settling at this temperature. The toluene phase is dried by azeotropic distillation and the solution thus obtained containing the 1-benzyl-4-cyano-4-phenylpiperidine base is added to a mixture of 2.83 kg of 95% sulfuric acid, 1.73 kg of glacial acetic acid and 3 l of toluene. The mixture thus obtained is heated for 6 hours, the heating is then stopped, the mixture is cooled to 60° C. and 3 l of water are added at this temperature. The mixture is allowed to cool to room temperature (about 20° C.) and is then poured into 8.65 l of 30% sodium hydroxide and 6.75 l of water. The temperature rises gradually to 75° C. The phases are separated by settling while hot, the organic phase is washed with water and dried, it is cooled to −5° C., a sodium methoxide solution prepared from 4.52 l of methanol and 532 g of sodium is added at this temperature, over one hour and with stirring, and, while maintaining the temperature at about 0° C., 1.85 kg of bromine are then added. The reaction mixture is left for 30 minutes at 0° C. and then overnight at room temperature, and is subsequently washed with water at 60° C. The toluene solution is dried azeotropically and is then concentrated by distilling off 75% of the amount of toluene used, and treated with 12 l of isopropyl ether. The resulting solution is cooled to 25° C. and then left to crystallize for 24 hours at room temperature and finally cooled to 0° C. The product thus precipitated is filtered off, washed with isopropyl ether and dried under vacuum at 50° C. 2.86 kg of 1-benzyl-4-methoxycarbonylamino-4-phenylpiperidine are thus obtained with an HPLC purity of 99%.

Yield: 92% calculated from the 1-benzyl-4-cyano-4-phenylpiperidine hydrochloride.

(b) 4-Methylamino-4-phenylpiperidine dioxalate 2.89 l of toluene are added to a solution of 5.54 kg of Vitride® at 70% in toluene, and the mixture is heated to 98° C. A solution, heated to 80° C., of 2.86 kg of 1-benzyl-4-methoxycarbonylamino-4-phenylpiperidine, obtained in step (a) in 1.3 l of toluene, is added to this solution over 3 hours at 98–100° C. with stirring. 3.92 l of a 5% sodium hydroxide solution are then added at 80° C. The mixture is allowed to cool to 55° C. and the organic phase is separated out by settling at this temperature and washed with water. By extracting the toluene phase with 823 g of formic acid in 8.64 l of water, 11.77 kg of a solution of 1-benzyl-4-methylamino-4-phenylpiperidine formate at pH 5.5 are obtained, and this solution is added to a mixture of 155.2 g of 5% Pd/BaSO$_4$ and 1.35 l of demineralized water pre-heated to 85° C., with stirring. 96.2 g of 5% of Pd/BaSO$_4$ and 417.4 g of formic acid are gradually added, still at 85° C. The mixture is heated for 12 hours at 85° C. and then allowed to cool to room temperature and 898.5 g of 95% sulfuric acid are added. The mixture is filtered and concentrated under vacuum down to about 6.5 l, 6.5 l of 4-methyl-2-pentanone are then added and the pH of the mixture is brought to 14 by addition of 30% sodium hydroxide. The aqueous phase is separated out by settling of the phases and re-extracted with 4-methyl-2-pentanone, and the combined organic phases are dried via azeotropic distillation. The solution thus obtained is poured into a solution of 1.57 kg of oxalic acid in 13.3 l of absolute ethanol and the precipitate thus obtained is filtered off, washed with ethanol and dried under vacuum at 70° C. 2.77 kg of 4-methylamino-4-phenylpiperidine dioxalate are thus obtained; m.p.= 214–215° C. Overall yield calculated from the starting 1-benzyl-4-cyano-4-phenylpiperidine hydrochloride: 78.5% of the theoretical amount.

EXAMPLE 3

4-Methylamino-4-phenylpiperidine base 6.3 g of potassium hydroxide and 15 ml of 4-methyl-2-pentanone are added at 20° C. to a solution of 7.5 g of 4-methylamino-4-phenylpiperidine dioxalate in 30 ml of water. The mixture is stirred, the phases are separated by settling and the aqueous phase is discarded. The organic phase is concentrated to dryness and the oily residue is taken up in 15 ml of toluene. The toluene solution is dried over magnesium sulfate. The minerals are filtered off and the precipitate is rinsed with 5 ml of toluene and concentrated to dryness. 3.8 g of a colorless oil, which is 4-methylamino-4-phenylpiperidine base, are thus obtained in a purity of greater than 97%.

EXAMPLE 4

4-Methylamino-4-phenylpiperidine sesquioxalate monohydrate

A solution of 2.1 kg of 1-benzyl-1-methoxycarbonylamino-4-phenylpiperidine, obtained according to step (a) of Example 2, in 5 l of tetrahydrofuran, is added, at reflux, to a mixture of 4.75 l of tetrahydrofuran and 368.5 g of lithium aluminum hydride. The mixture is cooled to 0° C. and 368 ml of water diluted in tetrahydrofuran and 368 ml of a 15% sodium hydroxide solution diluted in tetrahydrofuran are first added very slowly, and 736 ml of water diluted in tetrahydrofuran are finally added. The salts are removed by filtration and washed with tetrahydrofuran, the organic phases are combined and concentrated to dryness, the residue is taken up in 7 l of toluene and washed with water, and the toluene is concentrated to dryness. The oil is taken up in 12 l of acetone and 583 g of oxalic acid are added. The precipitate is filtered off and then used directly in 14 l of methanol. 280 g of 5% Pd/C containing 50% water are added. This mixture is hydrogenated at 45° C. and at ambient pressure for 24 hours, 3.36 l of water are then added and the reaction mixture is refluxed for 30 minutes. The mixture is filtered at this temperature, the methanol is removed by distillation and the essentially aqueous phase is heated to 95° C. 1.4 l of n-butanol are added while maintaining the temperature at 95° C., the mixture is then heated to reflux and cooled to 20° C., and the precipitate is filtered off, washed with a 9/1 butanol/water mixture (v/v) and dried at 60° C. under vacuum. 1.34 kg of 4-methylamino-4-phenylpiperidine sesquioxalate monohydrate are thus obtained; m.p.=252–254° C. (capillary).

EXAMPLE 5

4-Methylamino-4-phenylpiperidine dioxalate 7.0 l of a molar toluene solution of lithium aluminum hydride complexed with 2 mol of tetrahydrofuran are added over one hour to a solution of 1.5 kg of 1-benzyl-1-methoxycarbonylamino-4-phenylpiperidine in 8 l of toluene heated to reflux. Refluxing is maintained for 1 hour and the mixture is then cooled to 30° C. and 675 g of water are added very slowly. This mixture is cooled to 20° C. and the insoluble materials are then separated out by filtration.

By extraction of the toluene phase with 427.3 g of formic acid and 4.47 l of water, 6.05 kg of a solution of 1-benzyl-4-methylamino-4-phenylpiperidine formate are obtained, and this solution is added to a mixture of 81 g of 5% Pd/BaSO$_4$ and 0.7 l of water preheated to 85° C. with stirring. 50.4 g of 5% Pd/BaSO$_4$ and 219 g of formic acid are gradually added, still at 85° C. The mixture is heated for 12 hours at 85° C. and is then allowed to cool to room temperature and 470 g of 95% sulfuric acid are added. This mixture is filtered and concentrated under vacuum down to about 3.4 l, 3.4 l of methyl-2-pentanone are then added and the pH of the mixture is brought to 14 by addition of 30% sodium hydroxide. The aqueous phase is separated out by settling of the phases and re-extracted with 4-methyl-2-pentanone, and the combined organic phases are dried by azeotropic distillation. The solution thus obtained is poured into a solution of 0.82 kg of oxalic acid in 7 l of absolute ethanol, and the precipitate thus obtained is filtered off, washed with ethanol and dried under vacuum at 70° C. 1.52 kg of 4-methylamino-4-phenylpiperidine dioxalate are thus obtained; m.p.=214–215° C.

What is claimed is:

1. A process for preparing a 4-alkoxycarbonylamino-1-benzyl-4-phenylpiperidine of formula (I)

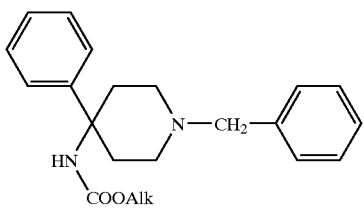

(I)

in which Alk represents an alkyl of 1 to 3 carbon atoms wherein 1-benzyl-4-cyano-4-phenylpiperidine of formula (II)

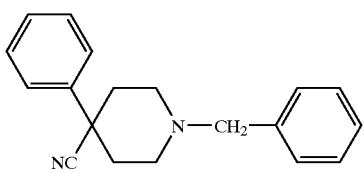

(II)

is hydrolyzed to the amide in acidic medium and the 1-benzyl-4-phenyl-4-piperidinecarboxamide thus obtained of formula (III)

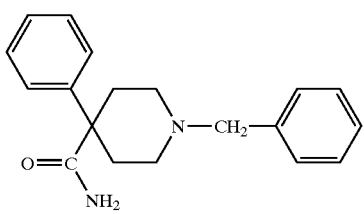

(III)

is treated with bromine in the presence of an alkali metal alkoxide of formula (iv)

Alk-OM (iv)

in which alk is a $(C_1-C_3)$alkyl and m is an alkali metal.

2. The process as claimed in claim 1 wherein the hydrolysis is performed with sulfuric acid and acetic acid in toluene at 80–100° C.

3. The process as claimed in claim 1 wherein sodium or potassium methoxide or sodium or potassium ethoxide is used as alkali metal alkoxide.

4. A process for preparing 4-methylamino-4-phenylpiperidine and its salts wherein:

(a) 1-benzyl-4-cyano-4-phenylpiperidine of formula (II) as claimed in claim 1 is hydrolyzed to the amide in acidic medium and the 1-benzyl-4-phenyl-4-piperidinecarboxamide of formula (III) as claimed in claim 1 is treated with bromine and an alkali metal $(C_1-C_3)$alkoxide; and then (b) the 4-$(C_1-C_3)$ alkoxycarbonylamino-1-benzyl-4-phenylpiperidine thus obtained is reduced with a metal hydride, which may be a mixed hydride, or with sodium bis(2-methoxyethoxy) aluminum hydride and the 1-benzyl-4-methylamino-4-phenylpiperidine thus obtained, optionally in the form of one of its salts, is debenzylated via catalytic reduction and the 4-methylamino-4-phenylpiperidine thus obtained is isolated either in free base form or in the form of one of its salts and is optionally converted into the free base.

5. The process as claimed in claim 4 wherein in step (b), the reduction is performed with lithium aluminum hydride or sodium bis(2-methoxyethoxy) aluminum hydride, and the debenzylation is performed either with formic acid or under a hydrogen atmosphere in the presence of palladium.

6. The process as claimed in claim 4 wherein:

(a') 1-benzyl-4-cyano-4-phenylpiperidine, prepared in situ via neutralization of its hydrochloride, is treated with 94–96% sulfuric acid and acetic acid in toluene at 80–100° C. and the 1-benzyl-4-phenyl-4-piperidinecarboxamide thus obtained is treated with bromine in the presence of sodium methoxide; and then (b') the 1-benzyl-4-methoxycarbonylamino-4-phenylpiperidine thus obtained is reduced with sodium bis(2-methoxyethoxy) aluminum hydride in toluene at a temperature of 90–100° C., the 1-benzyl-4-methylamino-4-phenylpiperidine thus obtained, or one of its salts, is debenzylated with formic acid in the presence of palladium, and the 4-methylamino-4-phenylpiperidine is isolated either in the form of the free base or in the form of one of its salts, which is optionally converted into the free base.

* * * * *